United States Patent [19]

Kneuper et al.

[11] Patent Number: 6,153,784
[45] Date of Patent: Nov. 28, 2000

[54] REMOVAL OF HALIDES FROM HALIDE-CONTAINING NITRILE MIXTURES

[75] Inventors: Heinz-Josef Kneuper, Mannheim; Hans-Jürgen Weyer, Bobenheim-Roxheim; Horst Neuhauser, Dudenhofen; Johann-Peter Melder, Neuhofen; Andreas Henne, Neustadt; Karl-Heinz Ross, Grünstadt; Rainer Becker, Bad Dürkheim, all of Germany

[73] Assignee: BASF Aktiengesellschaft, Ludwigshafen, Germany

[21] Appl. No.: 09/024,457

[22] Filed: Feb. 17, 1998

[30] Foreign Application Priority Data

Feb. 25, 1997 [DE] Germany .............. 197 07 509

[51] Int. Cl.$^7$ ................ C07C 253/34; C07C 211/09
[52] U.S. Cl. ............ 558/456; 558/342; 558/343; 558/401; 558/446; 558/454; 564/385; 564/415; 564/491; 564/492; 564/497; 564/498
[58] Field of Search .................. 558/342, 343, 558/401, 446, 454, 456; 564/385, 415, 491, 492, 497, 498

[56] References Cited

U.S. PATENT DOCUMENTS

| | | | |
|---|---|---|---|
| 2,570,794 | 10/1951 | Grigsby et al. | 260/465 |
| 2,695,912 | 11/1954 | Hartig | 260/465 |
| 3,853,947 | 12/1974 | Golser et al. | 260/465 |

FOREIGN PATENT DOCUMENTS

| | | |
|---|---|---|
| 920789 | 11/1954 | Germany . |
| 1046601 | 11/1957 | Germany . |
| 2211060 | 3/1972 | Germany . |

OTHER PUBLICATIONS

Derwent Abstract 89–041527 (JP 63196550; Aug. 15, 1988).
Derwent Abstract 91–183214 (JP 03112945; May 5, 1991).

*Primary Examiner*—Peter O'Sullivan
*Attorney, Agent, or Firm*—Keil & Weinkauf

[57] ABSTRACT

Halides are removed from halide-containing nitrile mixtures by (a) thermally treating the halide-containing nitrile mixture,
(b) subsequently adding a base to the thermally treated nitrile mixture and
(c) subsequently separating off the base from the nitrile mixture.

Amines are prepared by (A) reacting alkyl halides with metal cyanides in an at least two-phase reaction medium in the presence of halide-containing phase-transfer catalysts to give alkanenitriles,
(B) separating off the resulting halide-containing alkanenitrile mixture phase and
(C) further treating the halide-containing alkanenitrile mixture phase, as described in the stages
  (a)–(c) removing halides from halide-containing nitrile mixtures and
  (d) hydrogenating nitrites obtained in stage (c) to give amines, in the presence of suspended or fixed-bed catalysts.

8 Claims, No Drawings

REMOVAL OF HALIDES FROM HALIDE-CONTAINING NITRILE MIXTURES

The present invention relates to a process for removing halides from halide-containing nitrile mixtures and to a process for preparing amines from these halide-containing nitrile mixtures.

Aliphatic amines are frequently prepared by hydrogenating nitriles. The nitriles may be synthesized by the Kolbe method by reacting alkyl halides with metal cyanides. A corresponding process for preparing alkanenitriles is described, for example, in Organikum, organisch-chemisches Grund-praktikum [Foundations of practical organic chemistry], 16th Edition, VEB Deutscher Verlag der Wissenschaften, Berlin 1986, pages 210 to 213. The method of preparation results in the nitriles having a content of halides, which are derived, in particular, from tetraalkylammonium halides used as phase-transfer catalyst, if the nitriles are prepared in the presence of such catalysts. The resulting halides lead to severe corrosion of the reactors used. In addition, fixed-bed catalysts are deactivated by the halides, so that only batchwise hydrogenation is possible.

In order to be able to carry out the hydrogenation continuously on fixed-bed catalysts, it is necessary to remove the halides from the nitriles prior to the hydrogenation.

It is an object of the present invention to provide a process for removing halides from halide-containing nitrile mixtures which permits the subsequent preparation of amines from the nitrile mixtures.

We have found that this object is achieved by providing a process for removing halides from halide-containing nitrile mixtures by (a) thermally treating the halide-containing nitrile mixture, (b) subsequently adding a base to the thermally treated nitrile mixture and (c) subsequently separating off the base from the nitrile mixture.

It has been found that in the preparation of nitriles, in particular suberonitrile by reacting 1,6-dichlorohexane with aqueous cyanide solution, in the presence of tetraalkylammonium halides as phase-transfer catalyst, the resulting nitrile contains halide at from about 500 to 1000 ppm. The halide has tetraalkylammonium ions as counter ions and is thus a constituent of a phase-transfer catalyst. Obviously, this catalyst cannot be removed from the organic nitrile mixture by washing with water or bases, since it is soluble in both the aqueous and organic phases. The crude nitrile, in particular suberonitrile, can be distilled to separate off the halide and for further purification of the nitrile. However, significant amounts of halide, from about 400 to 500 ppm, have still been found in the distillate, so that neither washing with water or bases, nor distillation, successfully separates off halide.

According to the invention it has been found, however, that the halides may be removed by thermally treating the crude nitrile mixture and subsequently adding a base to the thermally treated nitrile mixture. Without being bound to the following description of the course of the reaction, it is assumed that tetraalkylammonium salts, under thermal treatment, eliminate olefins to form trialkylammonium hydrohalides. These are volatile, in contrast to tetraalkylammonium salts, since they dissociate into trialkylamine and hydrogen halide on heating. These two components are gaseous or volatile and can pass through a distillation, to reform trialkylammonium hydrohalide on condensation. However, the trialkylammonium hydrohalides present after the thermal treatment can be removed by reacting with a base and subsequently separating off the base from the nitrile mixture. The process according to the invention can decrease the halide content to a very low value, preferably below 10 ppm (limit of detection). The nitrile mixtures or nitriles thus obtained can be hydrogenated catalytically without the apparatuses used exhibiting corrosion or the catalysts being deactivated.

The thermal treatment in stage (a) is carried out in such a manner that halide-containing phase-transfer catalysts, in particular tetraalkylammonium halides, present in the halide-containing nitrile mixture, are converted into trialkylammonium hydrohalides. The thermal treatment is preferably carried out at from 50 to 350° C., particularly preferably from 150 to 300° C. for a period which is sufficient for the conversion of tetraalkylammonium halides into trialkylammonium hydrohalides. Preferably, the thermal treatment is a distillation at a pressure and temperature at which the nitrile present in the mixture is distilled. For example, a continuous distillation of suberonitrile is performed at a pressure at the top of the distillation of 50 mbar, a bottom temperature of from 227 to 230° C. and an overhead temperature of 163° C. Other possibilities for the thermal treatment are known to those skilled in the art.

After the thermal treatment, a base is added to the thermally treated nitrile mixture. As base, use is made of, for example, alkali metal hydroxides, alkali metal hydrogen carbonates or alkali metal carbonates, in particular in the form of aqueous solutions. Particularly preferably, use is made of the sodium or potassium compounds, the concentration of alkali metal hydroxide in the aqueous alkali metal hydroxide solution being preferably from 5 to 50, in particular from 10 to 30, % by weight. Aqueous solutions of alkali metal hydrogen carbonates or alkali metal carbonates are preferably concentrated, in particular saturated. The aqueous base solution is preferably added to the thermally treated nitrile mixture with stirring, in order to ensure good contact between the organic and aqueous phases. Trialkylammonium hydrohalides are deprotonated to form alkali metal halide, which is only water-soluble, and trialkylamines. To a very great extent, the alkali metal halide is present in the aqueous phase in this case, so that the halide content in the organic nitrile mixture phase decreases to below, preferably, 10 ppm.

In particular when concentrated base solutions are used, the phase separation into organic nitrile mixture phase and aqueous phase proceeds readily and virtually completely. The standing times, ie. the times required for the phase separation, are preferably in the range of minutes. Preferably, more than 80%, particularly preferably more than 90%, in particular 95% or more, of the aqueous solution is recovered. The aqueous base solution is added at a temperature at which nitrile saponification is completely or substantially prevented. Preferably, ambient temperature is employed. No nitrile saponification has been found in this case, which would be exhibited as an increase in the distillation residue on a subsequent distillation of the nitrile mixture.

The base used can also be a base present in the solid state, for example a basic ion-exchanger. Removal of the ion exchanger from the nitrile mixture is simple in this case, for example by decanting or filtering.

Preferably, the addition of a base in stage (b) is carried out using sodium hydroxide, sodium hydrogen carbonate or sodium carbonate or corresponding potassium salts in the form of a solution or in solid form.

The purified nitriles thus obtained, for example suberonitrile, can be hydrogenated on suspended catalysts or, in particular, on fixed-bed catalysts, without corrosion in the reactor or deactivation of the catalyst occurring. The invention also relates to a process for preparing amines from halide-containing nitrile mixtures by removing halides from the halide-containing nitrile mixtures as described in the abovementioned stages (a), (b) and (c) and subsequent hydrogenation of nitriles obtained in stage (c) to give amines, in the presence of suspended catalysts or fixed-bed catalysts (stage (d)). As suspended catalysts or fixed-bed catalysts, use can be made of all suitable catalysts. Preferably, the catalysts described in DE-A-44 46 893 are used. In particular, the catalyst used for the hydrogenation comprises nickel and/or cobalt and/or palladium and/or platinum and/or iron and/or ruthenium. Particularly preferably, the catalyst comprises 90% by weight of CoO, 5% by weight of $Mn_2O_3$, 3% by weight of $P_2O_5$ and 2% by weight of $Na_2O$.

Suitable reaction conditions for the hydrogenation are described, for example, in DE-A-44 46 893. The temperature is preferably from 60 to 160° C., particularly preferably from 90 to 130° C., the total pressure is preferably from 20 to 300 bar, particularly preferably from 150 to 250 bar, the molar ratio of nitrile groups to ammonia is preferably from 1:1 to 1:50, particularly preferably 1:5 to 1:20.

The hydrogenation may be carried out continuously or batchwise. Preferably, it is carried out continuously, in particular in the presence of a fixed-bed catalyst. Since fixed-bed catalysts can also be used for hydrogenating the nitrile mixtures purified according to the invention, without any risk of deactivation, the hydrogenation can be carried out continuously, and thus considerably more economically, than was possible hitherto.

The halide-containing nitrile mixtures used in the process according to the invention preferably originate from the reaction of alkyl halides with metal cyanides. The invention also relates to a process for preparing amines by (A) reacting alkyl halides with alkali metal cyanides in an at least two-phase reaction medium in the presence of halide-containing phase-transfer catalysts to give alkanenitriles, (B) separating off the resulting halide-containing alkanenitrile mixture phase and (C) further treating the halide-containing alkanenitrile mixture phase according to the stages (a) to (d), as described above.

Reacting alkyl halides with metal cyanides to give nitriles is generally known as the Kolbe nitrile synthesis. Preferably, primary or secondary, in particular primary, alkyl halides are used in this reaction. The alkyl halides here are preferably based on an aliphatic $C_{1-30}$, preferably $C_{1-20}$, particularly preferably $C_{2-18}$, in particular $C_{4-10}$ radical which is substituted by 1 to 5 halogens, and may be substituted by $C_{1-6}$alkyl, $C_{6-10}$aryl, $C_{1-6}$alkoxy, $C_{6-10}$aryloxy, COOH, OH or, as $C_{2-30}$, preferably $C_{2-20}$, particularly preferably $C_{2-18}$, in particular $C_{4-10}$ radical, may be interrupted by $C_{6-20}$aryl. Preferably the radical is substituted by 1 to 3, in particular 1 or 2, halogens. The halogens here are preferably chlorine or bromine, in particular chlorine. Preferably, none, or one to three, of said further substituents are present. Examples of suitable substituents are methyl, ethyl, propyl, butyl, pentyl, hexyl in the structurally isomeric forms thereof, phenyl, naphthyl, methoxy, ethoxy, propoxy, butoxy, pentoxy, hexoxy, phenyloxy, naphthyloxy. A phenyl- or naphthyl-substituted aliphatic $C_{1-20}$ radical is preferably a methyl radical, so that a benzyl or methylnaphthalene structure results. The aryl radicals, such as phenyl or naphthyl, may be additionally substituted by the abovementioned radicals, preferably alkoxy and alkyl, in particular $C_{1-6}$, specifically $C_{1-2}$alkoxy or alkyl, radicals. Examples of aliphatic $C_{2-20}$ radicals interrupted by $C_{6-20}$aryl are o-, m-, p-dimethylbenzene or corresponding diethyl or dipropyl compounds.

Preferably, the radical is a linear aliphatic $C_{1-20}$ radical which is substituted by a halogen at each end and has no other substituents. The radical here is preferably a linear aliphatic $C_{2-18}$, in particular $C_{4-10}$ radical.

The reaction is performed with metal cyanides, preferably alkali metal cyanides, in particular sodium cyanide. The at least two-phase reaction medium in this case preferentially exhibits an aqueous phase and an alkyl halide-containing organic phase; this is thus a two-phase reac-tion medium. The organic phase can additionally contain at least one further organic solvent which does not participate in the reaction.

The reaction is carried out in the presence of halide-containing phase-transfer catalysts, in particular alkylammonium halides. These have at least one $C_{1-30}$, preferably $C_{1-20}$, alkyl radical, and preferably have at least two, particularly preferably 3 or 4, of these alkyl radicals. They can have one $C_{8-24}$alkyl radical and one to three $C_{1-8}$alkyl radicals. The alkyl radicals, in particular methyl radicals, can be substituted by aromatic radicals. Thus, phenyl radicals can be bound to the nitrogen atom via alkylene radicals, but can also be directly bound. Examples of compounds of this type are benzyltrialkylammonium halides, such as benzyl-$C_{12-18}$-alkyldimethylammonium halides.

Particularly preferably, tetra-$C_{1-10}$-, in particular tetra-$C_{3-8}$-alkylammonium halides are used. Particular preference is given to the chlorides and bromides.

The halide-containing alkanenitrile mixtures obtained contain alkanenitriles which are based on the above-described alkyl halides, except that the halogens are replaced by cyano groups. The nitrile mixtures which can be used in the process according to the invention thus contain the compounds listed above, with the halogens being replaced by cyano groups.

Examples are dicyanopropane, dicyanobutane, dicyanopentane, dicyanohexane, dicyanoheptane, dicyanooctane, dicyanononane, dicyanodecane, o/m/p-alkoxyphenylacetonitrile, dialkoxyphenylacetonitrile, trialkoxyphenylacetonitrile.

The conditions in the reaction of the alkyl halides with metal cyanides are known in this case.

The halide-containing alkanenitrile mixture phase (stage B) obtained in the reaction is preferably removed by phase separation of the two-phase reaction medium, with or without the aqueous phase remaining in the organic phase subsequently being distilled off.

A process according to the invention for preparing amines, in particular aliphatic monoamines or aliphatic diamines, is carried out by reacting alkyl halides with metal cyanides as described in stage (A), separating off the resulting halide-containing alkanenitrile mixture phase in stage (B) by phase separation and subsequent initial-stage distillation, residues of the aqueous phase remaining in the organic phase being removed, distillation of the halide-containing alkanenitrile mixture in stage (a), adding an aqueous base solution to the thermally treated nitrile mixture in stage (b), separating off the base from the nitrile mixture by phase separation in stage (c), hydrogenating the nitriles obtained in stage (c) to give amines, in the presence of fixed-bed catalysts, and subsequent distillation of the resulting amines for their purification.

The examples illustrate the invention in more detail.

EXAMPLES

Example 1

Preparation of Suberonitrile

Suberonitrile was prepared continuously in a stirred tank cascade from 1,6-dichlorohexane and aqueous NaCN (molar ratio 1:2,02) at 100° C. in the presence of n-Bu$_4$NBr (3.2% by weight, based on the amount of 1,6-dichlorohexane used). After the synthesis, the phases were separated. The aqueous phase still contained about 2% by weight of NaCN and was treated with formaldehyde prior to disposal. The organic phase was washed batchwise 4 to 5 times with water. Initial-stage distillation was then performed to remove water remaining in the organic phase.

The suberonitrile mixture was then distilled in a continuous distillation at 50 mbar top pressure, from 227 to 230° C. bottom temperature and 163° C. overhead temperature. The suberonitrile thus purified still contained about 440 ppm of chloride. This distilled suberonitrile was used in the following studies.

Example 2

Purification of Suberonitrile 200 g of suberonitrile, which had been obtained as described in Example 1, and 700 g of the aqueous solutions, below, of NaOH, Na$_2$CO$_3$, NaHCO$_3$ or deionized water were stirred for 0.5 or 24 h. A phase separation was then performed; the standing time was determined. The proportion of the recovered aqueous phase and of the distillation residue obtained in a subsequent distillation was determined. This residue indicates whether suberonitrile was hydrolyzed by the extraction. The results are reported in Table 1 below.

The chloride content determined after the extraction was less than 10 ppm when NaOH, Na$_2$CO$_3$ and NaHCO$_3$ were used. The use of deionized water is described in Example 3.

Use of the abovementioned base solutions markedly decreased the standing time compared with the use of deionized water.

Example 3

Purification of Suberonitrile 60 kg of suberonitrile (chloride content 440 ppm) from Example 1 were extracted at 60° C. by stirring with 20 kg of water (1 h). After standing for 24 hours, 17 kg of water were separated off. The organic phase contained 70 ppm of chloride. A further 60 kg of suberonitrile were then extracted by stirring with 20 kg of water for 1 h and the phases were separated after 18 h. 20 kg of saturated NaHCO$_3$ solution were added to the organic phase and the mixture was extracted by stirring for 1 h. After the stirrer was shut off, the mixture was allowed to stand for 10 h and 20 kg of aqueous phase was separated off and discarded. Chloride content: <10 ppm. The two organic phases were combined (chloride content 30 ppm) and hydrogenated in a high-pressure reactor.

Example 4

Purification of Suberonitrile 5000 kg of suberonitrile from Example 1 were pumped with stirring at 25° C. to 2000 kg of 25% strength sodium hydroxide solution. The mixture was then stirred for 5 h at 25° C. After standing for approximately 5 hours and subsequent separation of the phases, the bottom aqueous phase was drained off and discarded and the top organic phase was taken for further processing.

Example 5

Continuous Hydrogenation of Suberonitrile Extracted with NaHCO$_3$ 500 ml/h of ammonia and 100 ml/h of suberonitrile were continuously run, at 90° C. and 200 bar hydrogen pressure, into a 1 liter capacity reactor, charged with 0.5 l of a fixed-bed cobalt catalyst. Suberonitrile which had a chloride content of 30 ppm was used, which was obtained as in Example 3. The high-pressure hydrogenation proceeded at 100° C. and a catalyst loading of 0.2 l/l h for 21 days with more than 99% conversion rate and 98% selectivity. No catalyst deactivation was observed.

Example 6

Continuous Hydrogenation of Suberonitrile Extracted with NaOH

Suberonitrile as described in Example 3 was hydrogenated in a high-pressure reactor which was charged with 60 l of catalyst. However, the suberonitrile was washed free from chloride (less than 10 ppm, previous content 370 ppm) using 10% strength NaOH solution. The high-pressure hydrogenation proceeded at 110° C. and a catalyst loading of 0.27 l/l h for 21 days with more than 99% conversion rate and 98% selectivity. No catalyst deactivation was observed.

COMPARATIVE EXAMPLE

Continuous Hydrogenation of Halogen-Containing Suberonitrile

The process as described in Example 5 was repeated, but 100 ml/h of suberonitrile (chloride content about 500 ppm) were run in continuously. After an operating time of 1 hour, 98% of the starting material were converted to the product diaminooctane. After 24 h, the conversion rate decreased to 11%.

| Temperature (° C.) | Stirring time (h) | Standing time (min) | Aqueous phase recovered (% by weight) | Residue (% by weight)** |
|---|---|---|---|---|
| NaOH 10% | | | | |
| 25° C. | 0.5 | 9 | 86 | |
| 50° C. | 0.5 | 5 | 86 | |
| 65° C. | 0.5 | 5 | 83 | 5.3 |
| NaOH 25% | | | | |
| 25° C. | 0.5 | 7 | 95 | 2.0 |
| 25° C. | 24 | 6 | 98 | 2.0 |
| Na$_2$CO$_3$ 10% | 0.5 | 6 | 97 | 1.3 |
| 25 % | | | | |
| NaHCO$_3$ saturated 60° C. | 0.5? | 600 | >99% | |
| Deionized water | | | | |
| 25° C. | 0.5 | >60 | 94 | |
| 78° C. | 0.5 | 20 | 87 | 2.4 |

**Residue at the starting product: 1.5–2.3% (blank value)

We claim:

1. A process for removing halides from halide-containing nitrile mixtures wherein the halide in the halide-containing nitrile mixture is present in whole or in part in the form of a halide-containing phase-transfer catalyst which comprises (a) thermally treating the halide-containing nitrile mixture, (b) subsequently adding a base selected from the group consisting of alkali metal hydroxides, alkali metal hydrogen carbonates or alkali metal carbonates in the form of an aqueous solution or in solid form to the thermally treated nitrile mixture and (c) subsequently separating off the base from the nitrile mixture.

2. A process as claimed in claim 1, wherein the thermal treatment is a distillation.

3. A process as claimed in claim 1, wherein the halide-containing phase-transfer catalyst is an alkylammonium halide.

4. A process as claimed in claim 1, wherein the base is a basic ion exchanger.

5. A process as claimed in claim 1, wherein the nitrile is based on an aliphatic $C_{1-30}$ radical which is substituted by 1 to 5 cyano groups and can be substituted by $C_{1-6}$alkyl, $C_{6-10}$aryl, $C_{1-6}$alkoxy, $C_{6-10}$aryloxy, COOH, OH or, as $C_{2-30}$ radical, can be interrupted by $C_{6-10}$aryl.

6. A process as claimed in claim 5, wherein the nitrile is a dinitrile which is based on a linear aliphatic $C_{1-20}$ radical which is substituted by a cyano group at each end.

7. A process for preparing amines from halide-containing nitrile mixtures by (a)–(c) removing halides from halide-containing nitrile mixtures according to claim 1 and (d) hydrogenating nitriles obtained in stage (c) to give amines, in the presence of suspended or fixed-bed catalysts.

8. A process for preparing amines by (A) reacting alkyl halides with metal cyanides in an at least two-phase reaction medium in the presence of halide-containing phase-transfer catalysts to give alkanenitriles, (B) separating off the resulting halide-containing alkanenitrile mixture phase and (C) further treating the halide-containing alkanenitrile mixture phase as described in the stages (a) to (d), as claimed in claim 7.

* * * * *

UNITED STATES PATENT AND TRADEMARK OFFICE
CERTIFICATE OF CORRECTION

PATENT NO. : 6,153,784
DATED : November 28, 2000
INVENTOR(S) : Kneuper et al.

It is certified that error appears in the above-identified patent and that said Letters Patent is hereby corrected as shown below:

Abstract,
Line 20, "nitrites" should be -- nitriles --.

Signed and Sealed this

Twenty-fifth Day of September, 2001

Attest:

NICHOLAS P. GODICI
Attesting Officer   Acting Director of the United States Patent and Trademark Office